(12) United States Patent
Blazecka et al.

(10) Patent No.: US 6,924,377 B2
(45) Date of Patent: Aug. 2, 2005

(54) PROCESS FOR PREPARING HIGHLY FUNCTIONALIZED γ-BUTYROLACTAMS AND γ-AMINO ACIDS

(75) Inventors: Peter G. Blazecka, Windsor (CA); James Guy Davidson, III, Howell, MI (US); Ji Zhang, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/421,350

(22) Filed: Apr. 23, 2003

(65) Prior Publication Data

US 2003/0236415 A1 Dec. 25, 2003

Related U.S. Application Data

(60) Provisional application No. 60/376,991, filed on Apr. 30, 2002.

(51) Int. Cl.[7] .................... C07D 207/24; C07C 229/00
(52) U.S. Cl. ...................... 548/543; 562/553
(58) Field of Search .......................... 548/543; 562/553

(56) References Cited

U.S. PATENT DOCUMENTS

| | | |
|---|---|---|
| 3,935,210 A | 1/1976 | Houlihan et al. |
| 6,265,591 B1 | 7/2001 | Anderson et al. |
| 6,306,910 B1 | 10/2001 | Magnus et al. |

FOREIGN PATENT DOCUMENTS

| | | |
|---|---|---|
| WO | WO93/23383 | 11/1993 |
| WO | WO00/76958 | 12/2000 |

OTHER PUBLICATIONS

Bourguignon, J.J, et al., Lactone Chemistry Synthesis of Beta–Substituted, Gamma–Functionalized Butanolides and Butenolides and Succinaldehydric Acids From Glyoxylic Acid, J. of Org Chem, American Chem Soc., Easton US, vol. 46(24), p. 4889–4894 (1981).

Ngwe, Hla, et al., A New Method for the preparation of A– and D–rings of phycocyanobilin using mucochloric acid as a starting material, Chem. Letters, vol. 8, 713–14 (1995).

International Search Report PCT/IB03/01646.

Database CA Online, Chemical Abstracts Service, Columbus, Ohio, US: Hachihama, Yoshikazu, et al., Syntheses of alpha–oxoglutarates and beta formylpropionates from furfural, retrieved from STN Database accession No. 52:55840, Abstract and Technology Reports of the Osaka University, vol. 7, 177–84 (1957).

Michael J. Mayer, Trip Report, Synthetic Pathways 9th Symposium on the Lastest Trends in Organic Synthesis, Albany Molecular Sciences Technical Report, vol. 5, No. 19, p. 9 (2001); also available at http://www.albmolecular.com.

Renzo Rossi, et al., Selective Synthesis ofUnsymmetrical, 3,4–Disubstituted and 4–Substituted 2(5H)–Furanones, Synlett, No. 12, p. 1749–1752 (2000).

Ahmend F. Abel–Magid, et al., Reductive Amination of Aldehydes and Ketones with Sodium Triacetoxyborohydride. Studies on Direct and Indirect Reductive Amination Procedures, J. Org. Chem., 61, p. 3849–3862 (1996).

Ji Zhang, et al., First Direct Reductive Amination of Mucochloric Acid, a Simple and Efficient Method to Prepare Highly Functionalized γ–Butyrolactams and γ–Amino Acids., Organic Letters, vol. 5(4), p. 553–556 (2003).

Sulikowski, G.A., et al., Inventigations into a Biomimetic Approach toward CP–225,917 and CP–263,114, J. Org. Chem., 65, p. 337–342 (2000).

H. Bistrzycki, et al., Ueber einige aliphatische γ–und aromatische o–Aldehydosauren, Chem. Ber., 34, p. 1010–1021 (1901).

H. Konig, et al., Pharmaceutical Chemistry Today—Changes, Problems, and Opportunities, Agnew Chem., vol. 19(10), p. 749–840 (1980).

G. Giambastiani, et al., A New Palladium–Catalyzed Intramolecular Allylation to Pyrrolidine–2–ones, J. Org. Chem., 63, p. 804 (1998).

R.K. Dieter, et al., Stereoselective Synthesis of 4–Alkylidene Pyrrolidinones and Pyrrolizidinones, Tetrahedorn Lett., 40, p. 4011 (1999).

C.H. Yoon, et al., Regio– and Stereocontrol Elements in Rh(II)–Catalyzed Intramolecular C–H Insertion of a–Diazo–a–(phenylsufonyl)–acetamides, vol. 3:22, p. 3539–3542 (2001).

Hoekstra, M.S., et al., Chemical Development of CI–1008, an Enantiomerically Pure Anticonvulsant, Org. Proc. Res. Dev. 1, p. 26–38 (1997).

Chen, Qing, Ha, et al., Chiral Source Optically Pure 5–(1–Menthyloxy–3,4–dichloro–2(5H)–furanone, Its Synthesis and Structure51(6), 622–4 (1993).

(Continued)

Primary Examiner—Paul A. Zucker
(74) Attorney, Agent, or Firm—Heidi M. Berven; Suzanne M. Harvey

(57) ABSTRACT

The invention relates to a process for preparing highly functionalized γ-butyrolactams and γ-amino acids by reductive amination of mucohalic acid or its derivatives, and discloses a process for preparing pregabalin, a GABA analog with desirable medicinal activity.

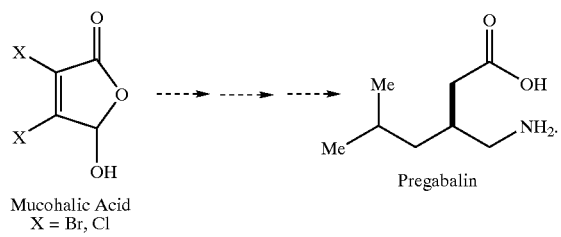

Mucohalic Acid
X = Br, Cl

Pregabalin

32 Claims, No Drawings

OTHER PUBLICATIONS

Wasserman, H.H., et al., Studies on the Mucohalic Acids, IV. Replacement of Halogen in the Pseudo Ester Seriers, J. Am. Chem. Soc., 76, p. 1242–1243 (1954).

Hill, H.B., et al., LXVII.—On Chlorpyromucic Acids, Am. Chem. J., 12, p. 22–51 (1890).

Chen, et al., Optically Pure Synthesis and a Novel Tandem Asymmetric Michael Addition–Elimination Reaction of Chiral 5–(1–Menthyloxy)–3,4–Dibromo–2–(5H)–Furanone, Youji Huzxue, 13(3), 299–300 (1993).

Jackson, P., H. Simonis: Neue Darstellungsweise der Mucobrom—und Mucochlor—Saure, Ber., 32, p. 2084–2085 (1899).

Von Dr. Karldury, Neue Synthese der Mucochlorsaure, Angew Chem, 72(22), p. 864–865 (1960).

Fishbein, P.L., et al., 7–Chloro–7–Cyanobicyclo[4.2.0]Octan–8–One, Org. Synth, 69, p. 205 (1990).

Ahmend F. Abel–Magid, et al., Reductive Amination of Aldehydes and Ketones By Using Soidum Triacetoxyborohydride, T. Letters, vol. 31, No. 39, pp, 5595–5598 (1990).

PROCESS FOR PREPARING HIGHLY FUNCTIONALIZED γ-BUTYROLACTAMS AND γ-AMINO ACIDS

CROSS REFERENCE TO RELATED APPLICATIONS

This application claims benefit of priority from U.S. Provisional Application No. 60/376,991, filed on Apr. 30, 2002.

FIELD OF THE INVENTION

The invention relates to a process for preparing highly functionalized γ-butyrolactams and γ-amino acids by reductive amination of mucohalic acid or its derivatives, and discloses a process for preparing pregabalin, a GABA analog with desirable medicinal activity.

BACKGROUND OF THE INVENTION

Pregabalin (S-3-Aminomethyl-5-methyl-hexanoic acid) is a 3-substituted γ-amino butyric acid (GABA) analog that exhibits an array of useful medicinal properties, as disclosed in WO 93/23383, as well as U.S. Pat. No. 6,306,910 and WO U.S. Pat. No. 00/76958, the latter two of which are assigned to the same assignee as the instant application.

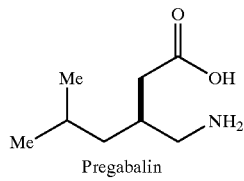

Pregabalin

Synthetic approaches to pregabalin, its racemate and related analogues such as 3-aminomethyl-5-methyl-octanoic acid, which has the structure

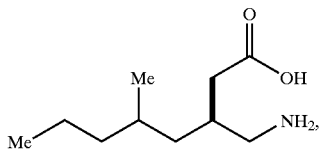

generally commence from a linear precursor. For instance, WO 93/23383 discloses a route commencing from 5-methyl-hexanoic acid that requires 8 transformations. A recently disclosed alternative strategy commences with the enantioselective conjugate addition of S-α methylbenzyl amine to 2-Methylene-succinic acid dimethyl ester (Michael J. Mayer, *Trip Report, Synthetic Pathways 9th Symposium on the Latest Trends in Organic Synthesis*, Albany Molecular Sciences Technical Report Vol. 5, No. 19 (2001), p. 9; also available at http://www.albmolecular.com. logical. net/features/tekreps/vol05 no19/ last visited Feb. 6, 2003). The reaction provides a mixture of diastereomers, which can be separated, and the requisite diastereomer is then converted to pregabalin via 6 additional steps.

A shortcoming of either of these approaches, particularly in scale-up and production contexts, is that they require a multitude of steps and purification operations. As a result, there is a need for a process for synthesizing pregabalin and other 3-substituted γ amino acids that minimizes the total number of synthetic transformations and simplifies purification steps.

SUMMARY OF THE INVENTION

These and other needs are met by the present invention which provides a process for preparing a compound of formula I

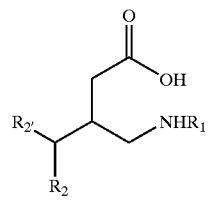

wherein: $R_1$ is H, $(C_1-C_8)$alkyl, $(C_3-C_7)$cycloalkyl, aryl, $(CH_2)_n$-aryl, heterocyclo, $(CH_2)_n$-heterocyclo, heteroaryl, or $(CH_2)_n$-heteroaryl, wherein n is 0, 1, 2, or 3; and $R_2$ and $R_{2'}$ are each independently H, straight or branched $(C_1-C_6)$alkyl, a straight or branched $(C_2-C_7)$alkenyl, $(C_3-C_7)$cycloalkyl, alkylcycloalkyl, alkylalkoxy, alkylphenyl, alkyphenoxy, phenyl or substituted phenyl;

comprising:

(a) treating mucochloric or mucobromic acid 1 wherein X is Cl or Br with R'OH, wherein R' is $(C_1-C_6)$alkyl, —$CH_2$-phenyl, or —$CH_2$-substituted phenyl, in the presence of acid to provide 2

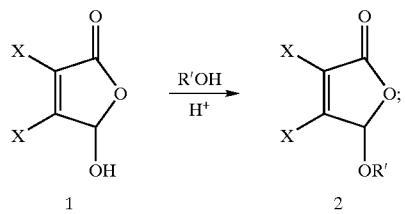

(b) conjugate addition of $R_2R_{2'}CHM_0$ wherein $R_2$ and $R_{2'}$ are as defined above and wherein $M_0$ is MgBr, CuBr, or $B(OH)_2$, to 2, to provide 3A

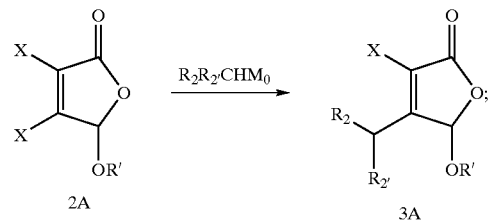

(c) hydrogenation of 3A to provide 4A

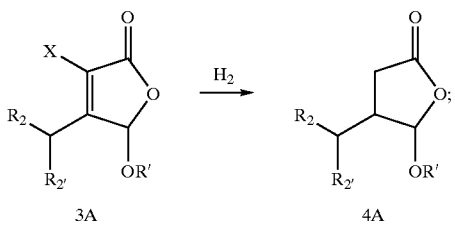

and (d) reductive amination of 4A under hydrogenation conditions using ammonium formate or $R_1NH_2$, wherein $R_1$ is $(C_1-C_8)$alkyl, $(C_3-C_7)$ cycloalkyl, aryl, $(CH_2)_n$-aryl, heterocyclo, $(CH_2)_n$-heterocyclo, heteroaryl, or $(CH_2)_n$-heteroaryl, wherein n is 0, 1, 2, or 3, followed by hydrolysis

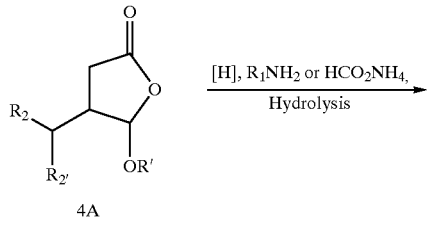

What is also provided is a process for preparing 3-Aminomethyl-5-methyl-hexanoic acid

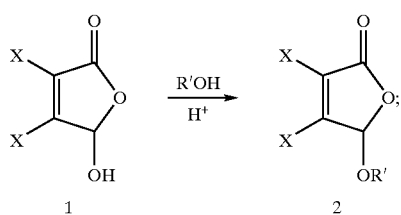

3-Aminomethyl-5-methyl-hexanoic acid comprising:

(a) treating mucochloric or mucobromic acid 1 wherein X is Cl or Br with R'OH, wherein R' is $(C_1-C_6)$alkyl or —$CH_2$-aryl, in the presence of acid, to provide 2

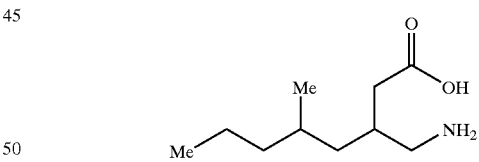

(b) conjugate addition of

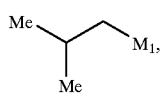

wherein $M_1$ is MgBr, CuBr, or

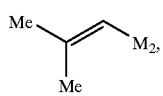

wherein $M_2$ is $B(OH)_2$, to 2 to provide 3B, wherein "- - -" is absent or is a bond;

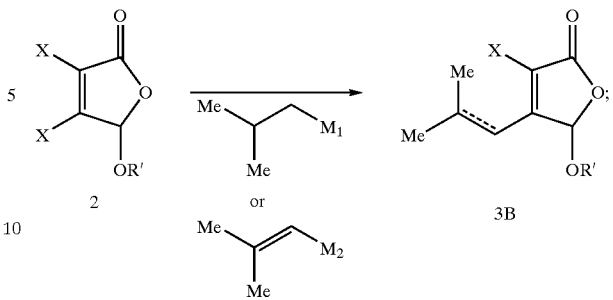

(c) hydrogenation of 3B to provide 4B

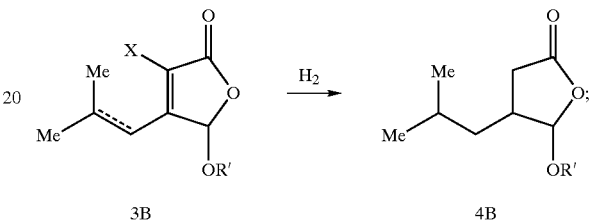

(d) reductive amination of 4B using ammonium formate, followed by hydrolysis

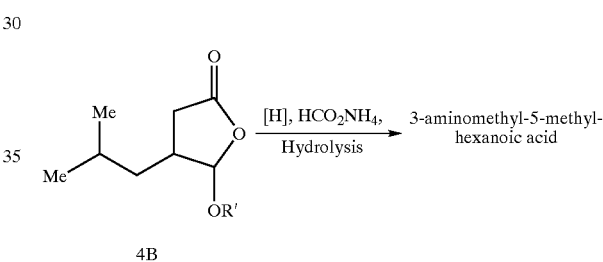

What is also provided is a process for preparing 3-aminomethyl-5-methyl-octanoic acid

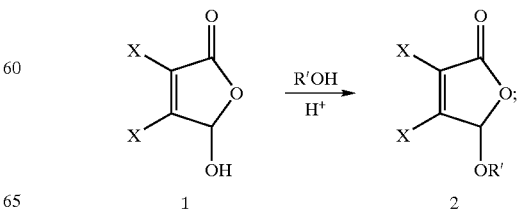

comprising:

(a) treating mucochloric or mucobromic acid 1 wherein X is Cl or Br with R'OH, wherein R' is $(C_1-C_6)$alkyl or —$CH_2$-aryl, in the presence of acid, to provide 2

(b) conjugate addition of

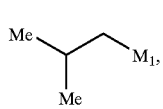

wherein $M_1$ is MgBr, CuBr, or

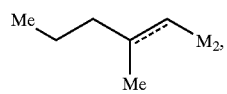

wherein $M_2$ is $B(OH)_2$, to 2 to provide 3BB, wherein "- - -" is absent or is a bond;

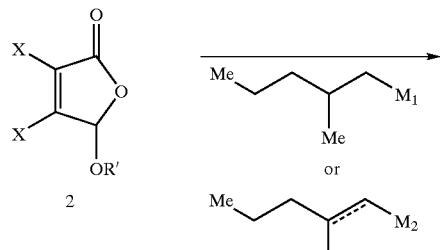

(c) hydrogenation of 3BB to provide 4BB

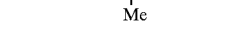

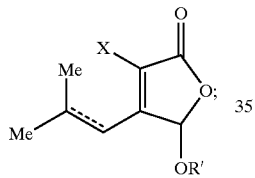

and (d) reductive amination of 4B using ammonium formate, followed by hydrolysis

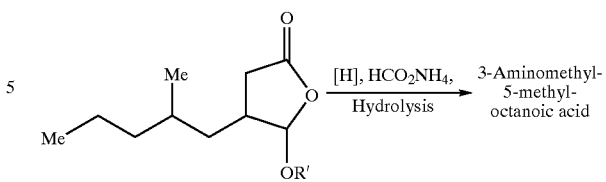

What is also provided is a process for preparing a compound of formula I

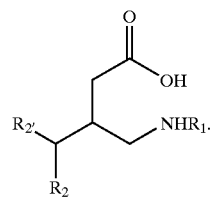

wherein: $R_1$ is H, $(C_1–C_8)$alkyl, $(C_3–C_7)$cycloalkyl, aryl, $(CH_2)_n$-aryl, heterocyclo, $(CH_2)_n$-heterocyclo, heteroaryl, or $(CH_2)_n$-heteroaryl, wherein n is 0, 1, 2, or 3; and $R_2$ and $R_{2'}$ are each independently H, straight or branched $(C_1–C_6)$alkyl, a straight or branched $(C_2–C_7)$alkenyl, $(C_3–C_7)$cycloalkyl, alkylcycloalkyl, alkylalkoxy, alkylphenyl, alkyphenoxy, phenyl or substituted phenyl;

comprising:

(a) reductive amination of mucochloric or mucobromic acid 1 wherein X is Cl or Br, using a reducing agent in the presence of ammonium formate or $R_1NH_2$, wherein $R_1$ is $(C_1–C_8)$alkyl, $(C_3–C_7)$cycloalkyl, aryl, $(CH_2)_n$-aryl, heterocyclo, $(CH_2)_n$-heterocyclo, heteroaryl, or $(CH_2)_n$-heteroaryl, wherein n is 0, 1, 2, or 3, and an acid catralyst, to provide 2C

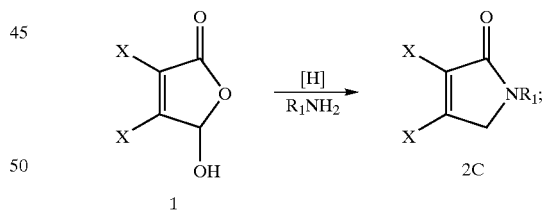

(b) conjugate addition of $R_2R_{2'}CHM_0$, wherein $M_0$ is MgBr, CuBr, or $B(OH)_2$, to 2C to provide 3C

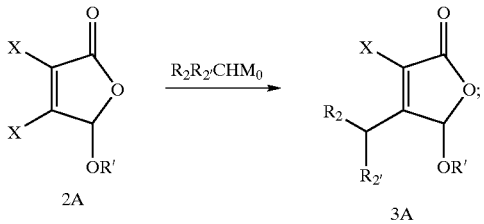

(c) hydrogenation of 3C to provide 4C

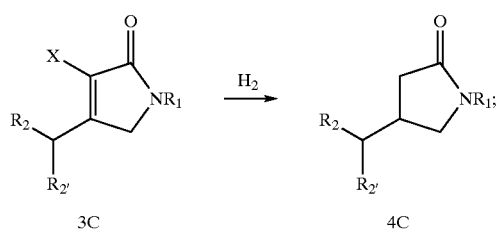

and (d) hydrolysis of 4C

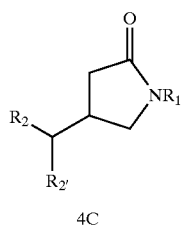

What is also provided is a process for preparing 3-Aminomethyl-5-methyl-hexanoic acid

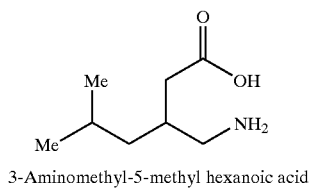

3-Aminomethyl-5-methyl hexanoic acid comprising:

(a) reductive amination of mucochloric or mucobromic acid 1 wherein X is Cl or Br using a reducing agent in the presence of benzylamine or 1-phenyl-ethylamine to provide 2D

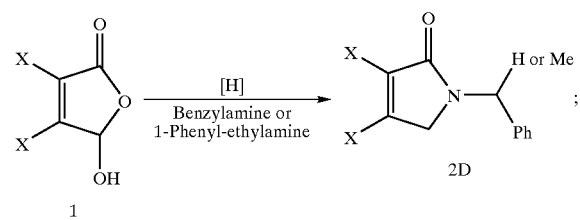

(b) conjugate addition of

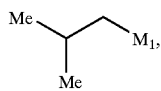

wherein $M_1$ is MgBr, CuBr, or

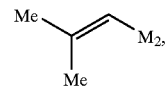

wherein $M_2$ is $B(OH)_2$, to 2D to provide 3D, wherein "- - -" is absent or is a bond;

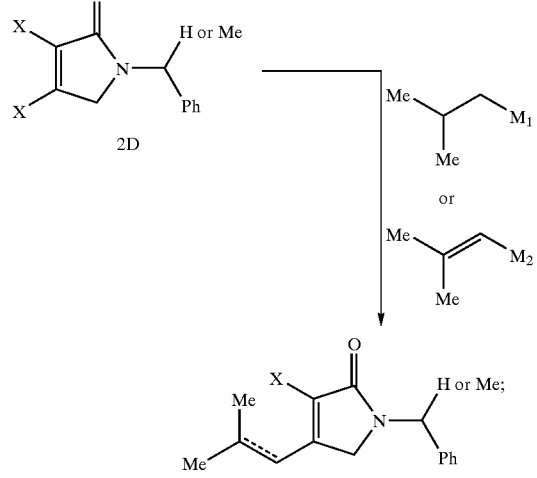

(c) hydrogenation of 3D to provide 4D

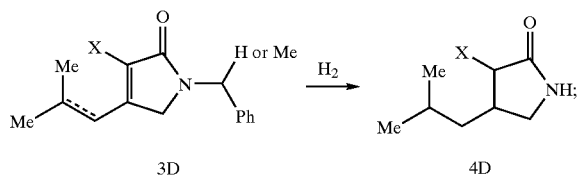

and
(d) hydrolysis of 4D

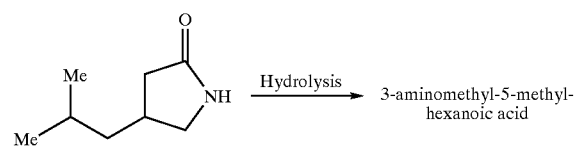

What is also provided is a process for preparing 3-aminomethyl-5-methyl-octanoic acid

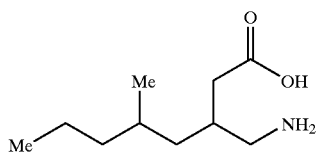

comprising:

(a) reductive amination of mucochloric or mucobromic acid 1 wherein X is Cl or Br using a reducing agent in the presence of benzylamine or 1-phenyl-ethylamine to provide 2D

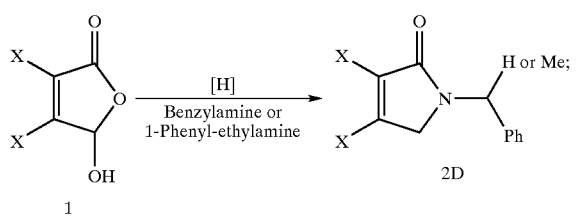

(b) conjugate addition of

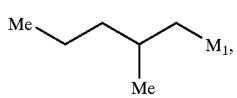

wherein $M_1$ is MgBr, CuBr, or

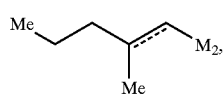

wherein $M_2$ is $B(OH)_2$, to 2D to provide 3DD, wherein "- - -" is absent or is a bond;

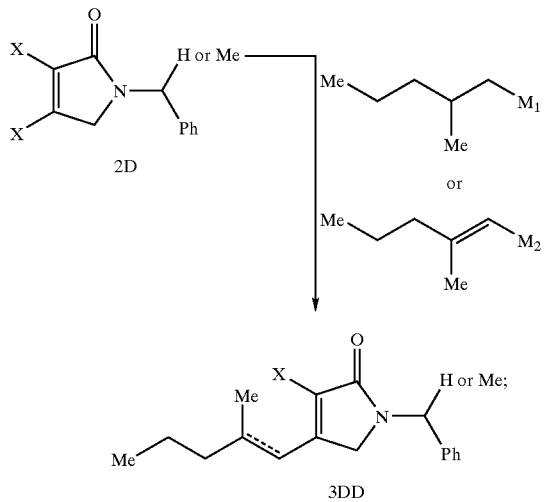

(c) hydrogenation of 3DD to provide 4DD

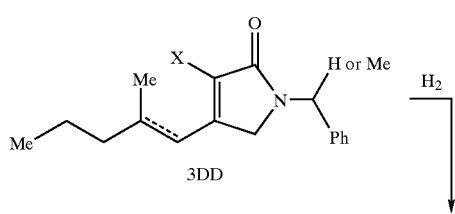

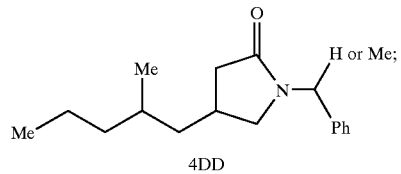

and (d) hydrolysis of 4DD

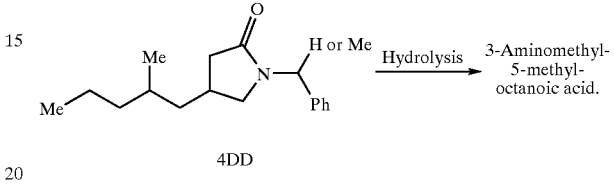

What is also provided is a process for reductively aminating mucohalic acid, comprising:

(a) contacting mucochloric or mucobromic acid I wherein X is Cl or Br with a reducing agent, an acid catalyst, and $R_3NH_2$, wherein $R_3$ is H, $(C_1-C_8)$alkyl, $(C_3-C_7)$cycloalkyl, aryl, $(CH_2)_n$-aryl, heterocyclo, $(CH_2)_n$-heterocyclo, heteroaryl, or $(CH_2)_n$-heteroaryl, wherein n is 0, 1, 2, or 3; to provide 2E

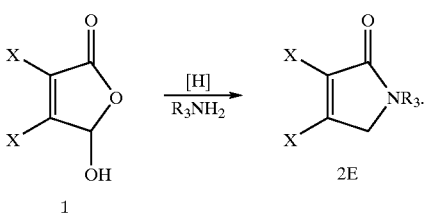

DETAILED DESCRIPTION OF THE INVENTION

The invention processes for preparing 3-substituted γ amino butyric acids disclosed herein possess a number of advantages. Firstly, they give rise to 3-substituted γ-amino butyric acids such as pregabalin, its racemate, or its analogues such as 3-aminomethyl-5-methyl-octanoic acid in a minimum number of steps and under mild conditions. Secondly, they make use of generally inexpensive and readily available reagents. Thirdly, they exploit the synthetic potential of mucohalic acid.

Mucochloric acid 1 (2,3-dichloro-4-oxo-2-butenoic acid) and mucobromic acid (2,3-dibromo4-oxo-2-butenoic acid) are commercially available and inexpensive starting materials. Both molecules are characterized by the presence of a carbon-carbon double bond with Z configuration, two halogen atoms, and two carbonyl groups. This high degree of functionality makes both mucochloric and mucobromic acid particularly useful building blocks for the synthesis of a variety of biologically active heterocycles, such as substituted 1,5-dihydropyrrol-2-ones, pyrrolidines, and γ-lactams, and γ-amino acids such as pregabalin.

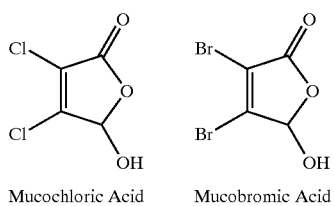

Mucochloric Acid   Mucobromic Acid

Mucobromic and mucochloric acid surprisingly have not been commonly employed in organic synthesis as C-4 building blocks. Presumably, this is because of the many reactive sites in the molecules, their poor stability under basic conditions, and the perception among those of ordinary skill in the art of the difficulties associated with the selective manipulation of the halogen atoms in the presence of the other functional groups.

In spite of these perceived difficulties, mucohalic acid is the keystone of the invention processes disclosed herein. As summarized in Scheme 1, the processes differ in the relative sequence of the reaction steps, but both rely on the use of mucohalic acid as a synthetic platform for the elaboration of the 3-substituted γ amino butyric acid framework. Thus, in Route A, protection of mucohalic acid in Step A provides the hemiacetal 2A. In Step B, Conjugate addition of $R_2R_2'M$ to 2A, followed by elimination of halide, provides conjugate addition product 3A. Hydrogenation of 3A in Step C to provide 4A, followed by reductive amination of 4C in Step D provides lactam 5A, which may undergo hydrolysis in situ or in a separate step to provide 3-substituted γ amino butyric acid I. In contrast, in Route A', reductive amination is the first step in the synthetic sequence (Step A'), followed by conjugate addition (Step B'), hydrogenation (Step C'), and hydrolysis (Step D').

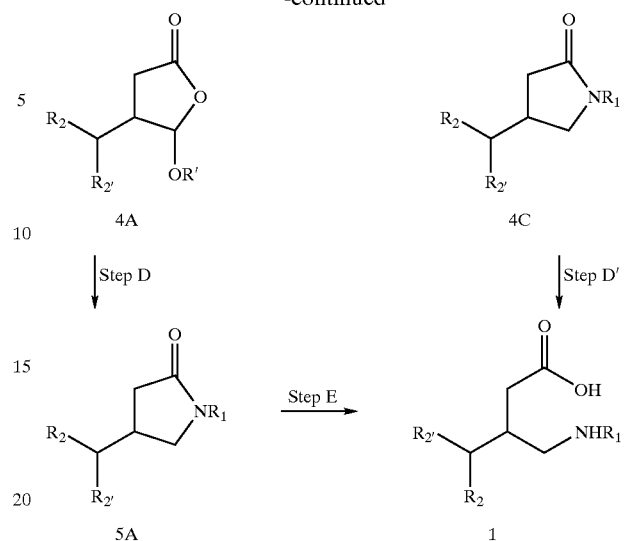

Pregabalin, its opposite enantiomer, or its racemate, is readily prepared by either of these routes. As depicted in Scheme 2, Route A, mucohalic acid is first converted to the O-benzyl acetal 2B. Organocuprate additon provides the conjugate addition product 3B. Hydrogenation and dehalogenation gives rise to 4B. Reductive amination under hydrogenation conditions gives rise to lactam 5B, which may be hydrolyzed under basic conditions to provide pregabalin or any of its analogues including 3-Aminomethyl-5-methyl-octanoic acid. Alternatively, as depicted in Route A' of Scheme 2, reductive amination of mucohalic acid in the first step using benzyl amine or 1-phenylethyl amine provides 2D. Conjugate addition, hydrogenation, and hydrolysis as described for Route A, provides the target compound.

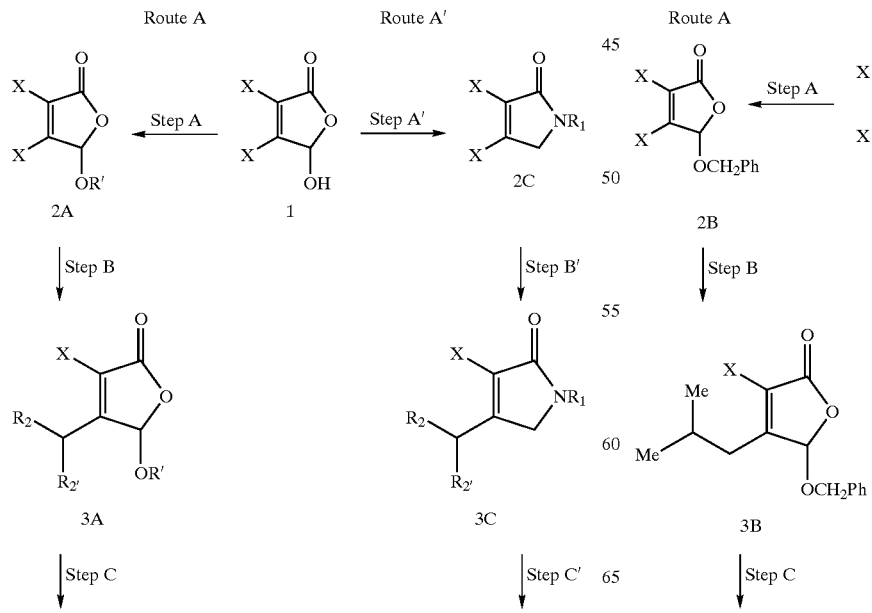

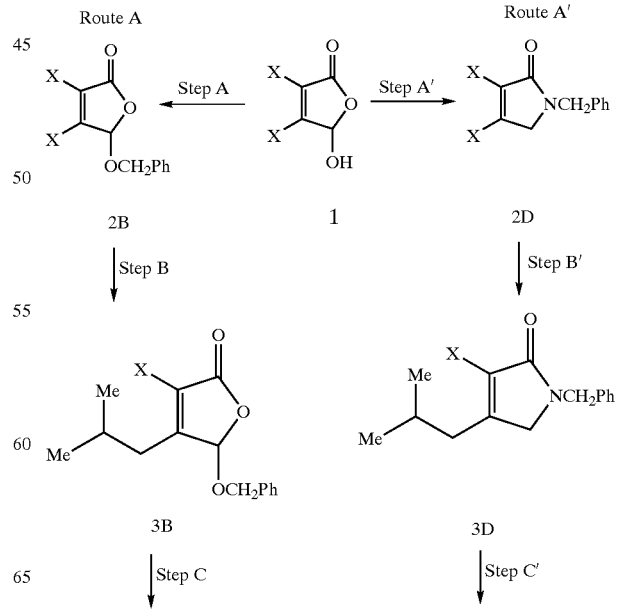

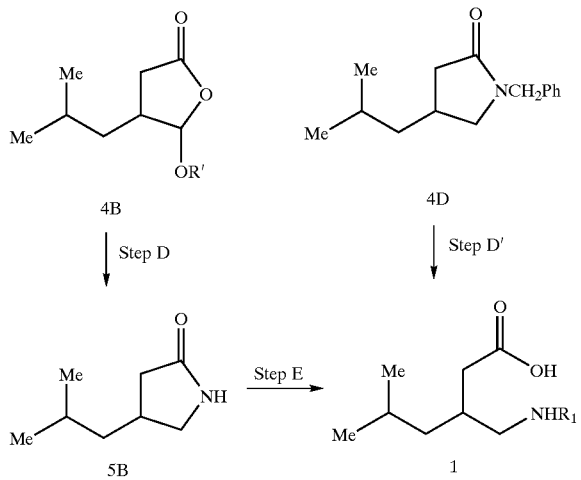

4B

Step D

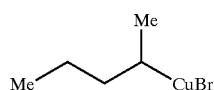

5B     Step E     1

This same methodology can be exploited to prepare the pregabalin analogue 3-aminomethyl-5-methyl-octanoic acid. All the steps are identical to the above, except that Step B or Step B' would require the use of or the like as described herein for the 1,4 conjugate addition/halide elimination reaction.

1. Definitions

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

Thus the term "alkyl" means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, n-hexyl, n-heptyl, and the like.

The term "alkenyl" means a straight or branched hydrocarbon radical having from 2 to 7 carbon atoms and includes, for instance, vinyl, allyl, 1-propenyl, 2-propenyl, 1-butenyl, 2-butenyl, 3-butenyl, 2-methyl-2-propenyl, 1-pentenyl, 2-pentenyl, 3-pentenyl, 4-pentenyl, 3-methyl-2-butenyl, 3-methyl-3-butenyl, 1-hexenyl, 2-hexenyl, 3-hexenyl, 4-hexenyl, 5-hexenyl, 4-methyl-3-pentenyl, 1-heptenyl, 2-heptenyl, 3-heptenyl, 2-methyl-1-hexenyl, 2-methyl-2-hexenyl, 3-methyl-2-hexenyl, 3-methyl-3-hexenyl, 3-methyl-1-hexenyl, 4-methyl-1-hexenyl, 5-methyl-1-hexenyl;

The term "cycloalkyl" means a hydrocarbon ring containing from 3 to 7 carbon atoms, for example, cyclopropyl, cyclobutyl, cyclopentyl, cyclohexyl, cycloheptyl, cyclooctyl, decalinyl, norpinanyl, and adamantyl. Where possible, the cycloalkyl group may contain double bonds, for example, 3-cyclohexen-1-yl. The cycloalkyl ring may be unsubstituted or substituted by one or more substituents selected from alkyl, alkoxy, thioalkoxy, hydroxy, thiol, nitro, halogen, amino, alkyl and dialkylamino, formyl, carboxyl, —CN, —NH—CO—R, —CO—NHR, —CO₂R, —COR, wherein R is alkyl, cycloalkyl, heterocycloalkyl, aryl, or heteroaryl, wherein alkyl, aryl, and heteroaryl are as defined herein.

The term "aryl" means a cyclic or polycyclic aromatic ring having from 5 to 12 carbon atoms, and being unsubstituted or substituted with one or more of the substituent groups recited above for alkyl, alkenyl, and alkynyl groups. Examples of aryl groups include phenyl, 2,6-dichlorophenyl, 3-methoxyphenyl, naphthyl, 4-thionaphthyl, tetralinyl, anthracinyl, phenanthrenyl, benzonaphthenyl, fluorenyl, 2-acetamidofluoren-9-yl, and 4'-bromobiphenyl.

The term "alkoxy" means a straight or branched hydrocarbon radical which has from 1 to 8 carbon atoms and is attached to oxygen. Alkoxy includes, for example, methoxy, ethoxy, n-propoxy, isopropoxy, n-butoxy, sec-butoxy, isobutoxy, tert-butoxu, n-pentoxy, n-hexoxy, n-heptoxy, and the like.

The term "alkylcycloalkyl" means a straight or branched hydrocarbon radical having from 1 to 8 carbon atoms as defined above attached to cycloalkyl group as defined above.

The term "alkylalkoxy", means a straight or branched hydrocarbon radical having from 1 to 8 carbon atoms as defined above attached to an alkoxy group as defined above.

The term "alkylphenyl" means a straight or branched hydrocarbon radical having from 1 to 8 carbon atoms as defined above attached to a phenyl or substituted phenyl group.

The term "alkyphenoxy" means a straight or branched hydrocarbon radical having from 1 to 8 carbon atoms as defined above attached to a phenoxy or substituted group.

The compounds prepared by the invention process may have one or more chiral centers and may exist in and be used or isolated in optically active and racemic forms. It is to be understood that the processes of the present invention can give rise to any racemic or optically-active forms, or mixtures thereof. It is to be further understood the products of the invention process can be isolated as racemic, enantiomeric, or diastereomeric forms, or mixtures thereof. Purification and characterization procedures for such products are known to those of ordinary skill in the art, and include recrystallization techniques, as well as chiral chromatographic separation procedures as well as other methods.

2. 3-Substituted γ Amino Butyric Acid Synthesis Via 5Alkoxy-3,4-dihalo-5H-furan-2-ones (Route A)

In Scheme 1, Step A of Route A, mucobromic or mucochloric acid is converted to the corresponding 5-alkoxy-3,4-dihalo-5H-furan-2-one 2A upon treatment with a $C_1$–$C_6$ alcohol or benzyl or substituted benzyl alcohol in the presence of acid. In a typical procedure, a toluene solution of I equivalent of mucohalic acid is combined with 1.5 equivalents of benzyl alcohol and 0.05 equivalent of p-toluene sulfonic acid. The mixture is then heated at reflux for 8 to 24 hours. The product furanone is typically obtained in high yield (85–90 percent).

In Step B of Route A, conjugate addition of an organocuprate reagent $R_2R_2$.CM to 2A, followed by halide elimination, provides the substituted furanone 3A. In a typical procedure, the organocuprate is generated in situ in the presence of N-methypyrrolidinone (NMP) from a commercially available Grignard reagent (e.g., an alkyl- aryl-, or alkylmagnesium bromide) and copper iodide. If the requisite Grignard reagent is not commercially available, it can be readily prepared from the corresponding organohalide compound using one of the many methods available to the skilled artisan. The furanone is then added to the organocuprate reagent over 5 to 10 minutes at −10 to 0° C., and the resulting mixture is allowed to warm to room temperature.

In Step C of Route A, hydrogenation of alkylfuranone 3A according to a method readily available to the skilled artisan provides dihydrofuranone 4A. In a typical procedure, the furanone is dissolved in THF, and combined with a tertiary amine base such as triethyl amine, and Pd/C. This mixture is hydrogenated in a high-pressure reactor until hydrogen uptake ceases.

In Step D of Route A, reductive amination of dihydrofuranone 4A with ammonium formate or $R_1NH_2$ gives rise to lactam 5A, which may be hydrolyzed in situ or isolated and converted to the 3-substituted γ amino butyric acid I in a separate step. In a typical procedure, dihydrofuranone 4A is combined in methanol with ammonium formate, triethyl amine, and Pd/C. This mixture is hydrogenated in a high pressure reactor until hydrogen uptake ceases to give rise to a mixture of the lactoam 5A and the desired ring-opened material I. Submission of the mixture to hydrolysis conditions known to the skilled artisan (for example, treatment with aqueous base), as depicted in Step E, gives rise to I.

Route A is readily adapted to the synthesis of pregabalin or 3-aminomethyl-5-methyl-octanoic acid. For pregabalin, step A remains the same. Step B requires the use of sec-butyl magnesium bromide to generate the necessary organocuprate. Alternatively, the sidechain can be attached in a Suzuki-type coupling procedure using

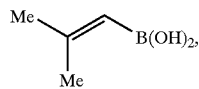

and a palladium catalyst. Steps C, D, and E remain the same. Similarly, as indicated earlier,

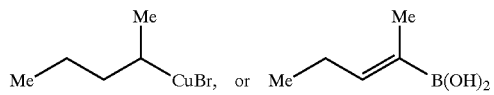

or the like as described herein, may be used to provide the precursor to 3-aminomethyl-5-methyl-octanoic acid. 3. 3-Substituted γ Amino Butyric Acid Synthesis Via 3,4-Dihalo-1-Substitued-1,5-dihydro-pyrrol-2-ones (Route A')

The first step in Route A' of Scheme I for the synthesis of 3-substituted γ amino butyric acid requires reductive amination of mucohalic acid to provide compound 2C.

A. Route A'/Step A: Reductive Amination of Mucohalic Acid

As indicated previously, mucobromic and mucochloric acid are not popular C-4 building blocks because of the many reactive sites in the molecules, their poor stability under basic conditions, and the perception among those of ordinary skill in the art of the difficulties associated with the selective manipulation of the halogen atoms in the presence of the other functionality. As an example, although it is known that in the presence of acetic acid, mucobromic or mucochloric acid may react with hydrazine or arylhydrazines to form pyridazinones (Scheme 3), the reaction conditions are severe: acetic acid as the solvent, a pH of 1 to 2, and temperatures between 60 and 120 ° C.

Scheme 3

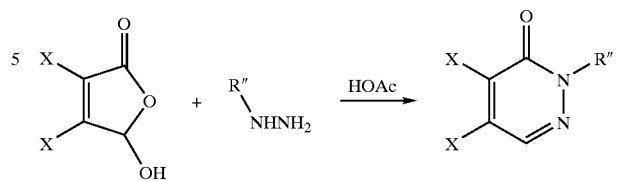

Other than this reported transformation, however, a manifold for the selective manipulation of the functional groups present in mucohalic acid is unknown.

i. Reagents

The reductive amination process described herein accommodates a wide variety of reagents and conditions.

Mucohalic Acid: To begin, either mucobromic or mucochloric acid are suitable for use in the reductive amination process.

Amine: Also, a wide variety of amines may be used in the reductive amination process, and are represented by the formula $R_1NH_2$, wherein $R_1$ is selected from hydrogen or $C_1$–$C_7$ alkyl or substituted $C_1$–$C_7$ alkyl, $C_3$–$C_{12}$ cycloalkyl or substituted $C_3$–$C_{12}$ cycloalkyl, $C_3$–$C_{12}$ heterocycloalkyl or substituted $C_3$–$C_{12}$ heterocycloalkyl, aryl or substituted aryl, or heteroaryl or substituted heteroaryl.

The primary or secondary alkyl, cycloalkyl, heterocycloalkyl, aryl, or heteroaryl amine used in the invention can be substituted with one or more groups selected from halo, hydroxy, $C_1$–$C_6$ alkoxy, carboxy, $C_1$–$C_6$ alkoxycarbonyl, aminocarbonyl, halomethyl, dihalomethyl, trihalomethyl, haloethyl, dihaloethyl, trihaloethyl, tetrahaloethyl, pentahaloethyl, thiol, ($C_1$–$C_4$)alkylsulfanyl, ($C_1$–$C_4$) alkylsulfinyl, and aminosulfonyl, Examples of substituted alkyl groups include fluoromethyl, difluoromethyl, trifluoromethyl, tribromomethyl, hydroxymethyl, 3-methoxypropyl, 3-carboxypentyl, 3,5-dibromo-6-aminocarbonyldecyl, and 4-ethylsulfinyloctyl. Examples of substituted alkenyl groups include 2-bromoethenyl, 1-amino-2-propen-1-yl, 3-hydroxypent-2-en-1-yl, 4-methoxycarbonyl-hex-2-en-1-yl, and 2-nitro-3-bromo4-iodo-oct-5-en-1-yl. Typical substituted alkynyl groups include 2-hydroxyethynyl, 3-dimethylamino-hex-5-yn-1-yl, and 2-cyano-hept-3-yn-1-yl.

The amine used in the reductive amination process may be an amino acid or its corresponding ester. Typical amino acids include L-lysine, L-alanine, L-arginine, L-aspartic acid, N-alpha-benzyloxycarbonyl-L-arginine, L-citrulline, gamma-L-glutamic acid, L-glycine, L-histidine, L-hydroxyproline, L-isoleucine, L-leucine, L-lysine, L-methionine, L-ornithine, L-phenylalanine, L-proline, L-pyroglutamic acid, L-serine, L-tryptophan, L-tyrosine, L-valine. The amine may also be a carboxy terminal-linked peptide having 1 to 10 amino acids or an addition salt thereof. Such peptides may include L-arginyl-L-arginine, N-benzyloxycarbonyl-glycyl-L-proline, L-glutaryl-glycyl-arginine, glycyl-glycine, glycyl-L-phenylalanine, glycyl-L-proline, and L-seryl-L-tyrosine, as well as others.

The amine used in the reductive amination process of the present invention may have one or more chiral centers and may exist in and be used or isolated in optically active and racemic forms. It is to be understood that the process of the present invention can employ any racemic, optically-active, polymorphic, geometric, or stereoisomeric form, or mixtures thereof, of an amine. It is to be further understood the products of the reductive amination process can be isolated as racemic, optically-active, polymorphic, geometric, or stereoisomeric forms, or mixtures thereof. Purification and characterization procedures for such products are known to those of ordinary skill in the art, and include recrystallization techniques, as well as chiral chromatographic separation procedures as well as other methods.

However, typically, benzyl amine or S-1-phenyl-ethyl amine is used.

Reducing Agent: A number of reducing agents can be used in the reductive amination process of the present invention. These reducing agents include sodium triacetoxy borohydride, sodium cyanoborohydride, triethyl silane, $Ti(OiPr)_4/NaBH_3CN$, borohydride exchange resin, Zn/acetic acid, sodium borohydride/magnesium perchlorate, or zinc borohydride/zinc chloride. Preferably, the reducing agent is sodium triacetoxyborohydride.

Acid Catalyst: A variety of acid catalysts can be used in the reductive amination process of the present invention. The acid may be a Bronsted, or protic, acid, or a Lewis, or non-protic, acid. Examples of protic acids suitable for use in the reductive amination process of the present invention include acetic acid, trichloroacetic acid, trifluoroacetic acid, or formic acid. Examples of non-protic acids suitable for use in the reductive amination process of the instant application include magnesium chloride, magnesium triflate, boron trifluoride etherate, $AlCl_3$, $FeCl_3$, $ZnCl_2$, $AlBr_3$, $ZnBr_2$, $TiCl_4$, $SiCl_4$ and $SnCl_4$.

ii. Procedure and Stoichiometry

In the reductive amination process of the present invention, the mucohalic acid is contacted with the amine, reducing agent, and acid catalyst. "Contacted" means that the reaction components are typically mixed in a liquid to form a homogeneous or heterogeneous mixture. The liquid employed in the reductive amination process of the present invention is selected from a polar aprotic solvent. Preferably, the polar aprotic solvent is selected from tetrahydrofuran, acetonitrile, nitromethane, chloroform, methylene chloride, monochloro ethane, 1,1, or 1,2 dichloroethane, 1,1,1 or 1,1,2 tricholoroethane, or 1,1,1,2, or 1,1,2,2 tetrachloroethane. More preferred solvents include methylene chloride or chloroform. Mixtures of solvents can also be used.

The molar equivalents of each of the reaction components (i.e., mucohalic acid, amine, reducing agent, and acid catalyst) used in the reductive amination process of the instant application are:
 (a) 1 equivalent of mucohalic acid;
 (b) 1 to 5 equivalents of amine;
 (c) 1 to 10 equivalents of reducing agent; and
 (d) sufficient acid catalyst to maintain a pH of about 2 to about 7.

More preferably, the molar equivalents of each of the reaction components (i.e., mucohalic acid, amine, reducing agent, and acid catalyst) used in the reductive amination process if the instant application are:
 (a) 1 equivalent of mucohalic acid;
 (b) 1 to 3 equivalents of amine;
 (c) 1 to 5 equivalents of reducing agent; and
 (d) sufficient acid catalyst to maintain a pH of about 3 to about 6.

Most preferably, the molar equivalents of each of the reaction components (i.e., mucohalic acid, amine, reducing agent, and acid catalyst) used in the reductive amination process if the instant application are:
 (a) 1 equivalent of mucohalic acid;
 (b) 1 to 2 equivalents of amine;
 (c) 1 to 3 equivalents of reducing agent; and
 (d) sufficient acid catalyst to maintain a pH of about 4 to about 5.

In the reductive amination process of the present invention, the initial concentration of mucohalic acid in the polar aprotic solvent is typically 0.1 to 0.5 M. More preferably, it is 0.15 to 0.45 M. Most preferably, it is 0.2 to 0.3 M.

In the reductive amination process of the present invention, the temperature is typically from about −25° C. to about 50° C., with lower temperatures being more suitable for mucobromic acid and higher temperatures being more suitable for mucochloric acid. When mucochloric acid is used, the temperature is more preferably from about about 0° C. to about 40° C., and most preferably from about 10° C. to about 30° C.

In the reductive amination process of the present invention, reaction times are typically from about 30 minutes to about 5 days; more preferably, from about 1 hour to 3 days; and most preferably, from about 6 hours to 48 hours.

To demonstrate the present invention process, the reactions of mucobromic or mucochloric acid with aniline or benzylamine in acetic acid were investigated (Table 4). A mixture of dichloromethane and acetic acid (1:1 v/v) was chosen as the solvent to maintain the stability and solubility of both starting materials. Sodium triacetoxyborohydride was used as the reducing agent and the reactions were conducted at room temperature. Initially γ-lactam 7 was isolated in 46% yield, but a solvent screen illustrated that 7 could be obtained in 65 to 75% yield once the amount of acetic acid was reduced.

TABLE 4

Reductive amination in different solvents.[a]

| entry | Solvent | Yield (%) |
|---|---|---|
| 1 | $CH_2Cl_2$:HOAc (1:1) | 46 |
| 2 | 1,4-dioxane | 48 |
| 3 | THF | 52 |
| 4 | $CH_3CN$ | 49 |
| 5 | DCE | 68 |
| 6 | $CHCl_3$ | 66 |
| 7 | $CH_3NO_2$ | 35 |
| 8 | $CHCl_3$ | 76 |

[a]Reaction conditions for entries 1, 2 and 6: 1 equiv of mucochloric acid, 1.1 equiv. of "aniline", 1.5 equiv of $NaBH(OAc)_3$, $CHCl_3$ (cat. HOAc), under $N_2$ for 24 h. Reaction conditions for entries 3–5, 7–8: 1 equiv of mucochloric acid, 1.0 equiv. of "aniline", 3.0 equiv of $NaBH(OAc)_3$, $CH_2Cl_2$:HOAc (5:3 v/v), under $N_2$ for 24 h. The reaction time was not optimized. Products were isolated and purified by silica gel chromatography and/or crystallization. Products are estimated to be >95% pure by $^1H$ NMR and elemental analysis. All compounds gave satisfactory elemental analysis data.

The invention process has been further extended to anilines, with electron-donating, electron-withdrawing and neutral substituents, as well as an heteroaromatic amine system (table 5). Electron-deficient anilines (entries 3, 4 and 9) and electron-rich anilines (entries 2, 5 and 7) reacted with almost equal facility and the heteroaromatic amine (entry 6) also underwent selective reaction with reasonable yield

TABLE 5

Reductive amination with different "anilines".[a]

| Entry | "Aniline" | Product | Yield (%) | Entry | "Aniline" | Product | Yield (%) |
|---|---|---|---|---|---|---|---|
| 1 | aniline | 3,4-dichloro-1-phenyl-pyrrolone | 50 | 5 | 3-hydroxyaniline | 3,4-dichloro-1-(3-hydroxyphenyl)-pyrrolidinone | 40 |
| 2 | 3,5-dimethoxyaniline | 3,4-dichloro-1-(3,5-dimethoxyphenyl)-pyrrolone | 55 | 6 | 2-aminopyridine | 3,4-dichloro-1-(pyridin-2-yl)-pyrrolone | 55 |
| 3 | 3-chloroaniline | 3,4-dichloro-1-(3-chlorophenyl)-pyrrolone | 65 | 7 | 3-methoxyaniline | 3,4-dichloro-1-(3-methoxyphenyl)-pyrrolone | 60 |
| 4 | 3-nitroaniline | 3,4-dichloro-1-(3-nitrophenyl)-pyrrolone | 42 | 8 | 4-aminoacetophenone | 3,4-dichloro-1-(4-acetylphenyl)-pyrrolone | 68 |
| 5 | 3-hydroxyaniline | 3,4-dichloro-1-(3-hydroxyphenyl)-pyrrolone | 40 | 9 | 3-aminobenzonitrile | 3,4-dichloro-1-(3-cyanophenyl)-pyrrolone | 75 |
| 6 | 2-aminopyridine | 3,4-dichloro-1-(pyridin-2-yl)-pyrrolone | 55 | 10 | 4-aminobenzoic acid | 3,4-dichloro-1-(4-carboxyphenyl)-pyrrolidinone | 20 |

[a] Reaction conditions for entries 1, 2 and 6: 1 equiv mucochloric acid, 1.1 equiv. of "aniline", 1.5 equiv of NaBH(OAc)$_3$, CHCl$_3$ (cat. HOAc), under N$_2$ for 24 h. Reaction conditions for entries 3–5, 7–10: 1 equiv of mucochloric acid, 1.0 equiv of "aniline", 3.0 equiv NaBH(OAc)$_3$, CH$_2$Cl$_2$:HOAc (5:3 v/v), under N$_2$ for 24 h. The reaction time was not optimized. Products were isolated and purified by silica gel chromatography and/or crystallization. Products are estimated to be >95% pure by $^1$H NMR and elemental analysis. All compounds gave satisfactory elemental analysis data.

Mucochloric acid (1) can exist as the open or cyclic form (Scheme 6). However, the ultraviolet spectrum in CHCl$_3$ indicates 1 exists predominantly in the lactone form. Additional spectral data, i.e. vibrational (IR, Raman) and others (NMR and NQR) suggest that the lactone is the dominant form in both the liquid and solid states. Experimental results further support these observations.

Scheme 6
Equilibria of Mucochloric and Mucobromic Acids.

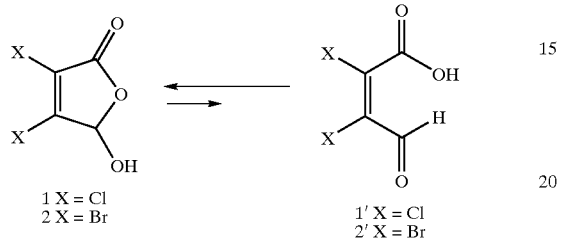

1 X = Cl
2 X = Br

1' X = Cl
2' X = Br

The proposed mechanism for the reductive amination process is depicted in Scheme 7. Thus, protonation of the aldehyde pushes the equilibrium in favor of the open-form aldehyde. Reductive amination of the aldehyde moiety, followed by ring closure and loss of water, provides the cyclic lactam.

Scheme 7.
Proposed mechanism of reductive amination.

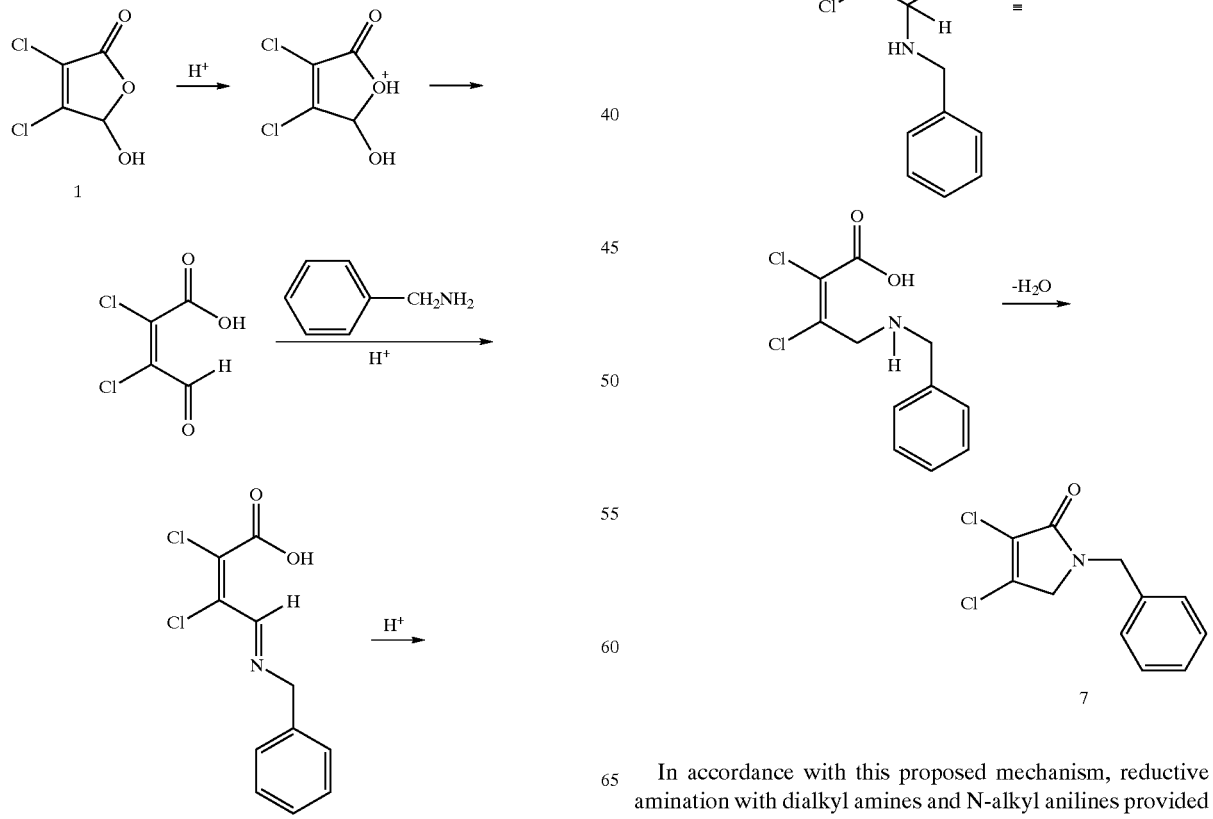

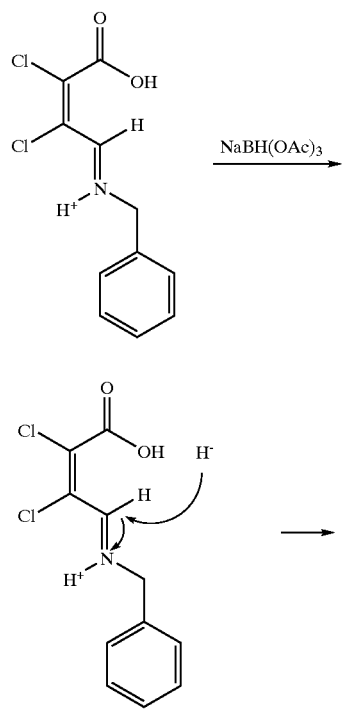

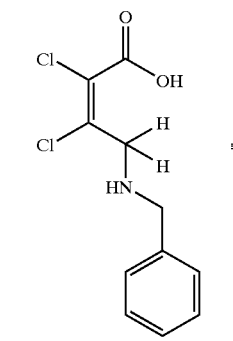

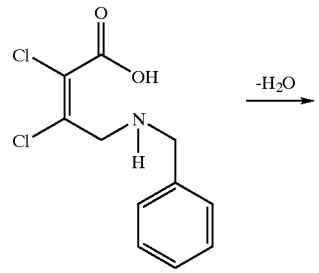

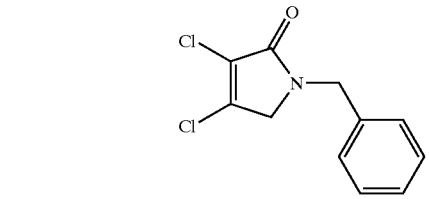

7

In accordance with this proposed mechanism, reductive amination with dialkyl amines and N-alkyl anilines provided substituted αβ-unsaturated γ-amino acids. All the attempts were successful and all products were isolated in acceptable yield. (Table 8).

TABLE 8

Reductive amination with different amines.[a]

[Scheme: dichloro-hydroxy-furanone 1 + amine → (NaBH(OAc)₃, Solvent) → product]

| Entry | amine | product | yield (%) |
|---|---|---|---|
| 1 | ethylamine (CH₃CH₂NH₂) | N-ethyl-3,4-dichloro-1,5-dihydropyrrol-2-one | 67 |
| 2 | pyrrolidine | acyclic pyrrolidinyl acid | 20 |
| 3 | N-methylaniline (PhNHCH₃) | acyclic N-methyl-N-phenyl amino acid | 48 |
| 4 | α-methylbenzylamine (H₂N-CH(R)-Ph) | N-(1-phenylethyl)-3,4-dichloro-1,5-dihydropyrrol-2-one | 89 |
| 5[b] | HCO-ONH₄ (ammonium formate) | lactam 8 / lactone 9 | 50/82 |
| 6 | CH₃CO-ONH₄ (ammonium acetate) | lactone 9 | 80 |
| 7 | H₂N-CH(Ph)-CH₂OH (phenylglycinol) | 85: N-(2-hydroxy-1-phenylethyl)-3,4-dichloro-1,5-dihydropyrrol-2-one | — |

[a]Reaction conditions: 1 equiv of mucochloric acid, 1.1 equiv. of amine, 1.5 equiv of NaBH(OAc)₃, CHCl₃ (cat. HOAc), under N₂ for 24 h. The reaction time was not optimized. Products were isolated and purified by silica gel chromatography and/or crystallization. Products are estimated to be >95% pure by ¹H NMR and elemental analysis. All compounds gave satisfactory elemental analysis data.
[b]This reaction provides a effective method of obtaining substituted γ-butyrolactones.

Interestingly, attempted reductive aminations with ammonium formate provided not the expected lactam 8, but instead, lactone 9, in 50% yield. When the reaction was repeated without adding ammonium formate, the yield of 9 increased to 82%. Also, when ammonium acetate was used, the reaction gave lactone 9 in 80% yield.

In summary, Step A' of Scheme 1, Route A' represents a simple, efficient and selective method to prepare N-benzyl-3,4-dichloro-1,5-dihydropyrrol-2-one, N-aryl (or alkyl)-3,4-dichloro-1,5-dihydropyrrol-2-ones and substituted γ-amino acids. These products possess a geometrically defined tetrasubstituted olefin, two differentiated vinyl halides and an acidic sight, and could be used in the synthesis of a variety of compounds.

B. Route A'/Steps B, C, and D

Steps B, C, and D of Route A' are as provided for Steps B, C, and E of Route A.

The following examples are intended to illustrate various embodiments of the invention and are not intended to restrict the scope thereof.

EXAMPLES

Route A Scheme 2

Step A: 5-Benzyloxy-3,4-dihalo-5H-furan-2-one.

Mucohalic acid (0.4–0.6 mol, I equivalent), benzyl alcohol (1.5 equivalents), and para-toluenesulfonic acid (0.05 equivalent) were combined in 1000 mL toluene and in an apparatus equipped with a Dean Stark Strap. The mixture was heated at reflux until water collection in the Dean Stark Trap had ceased. The mixture was then cooled to room temperature. The toluene was removed in vacuo at 35–40° C. to leave the crude product as a very pale amber oil. The crude material was purified by column chromatography on silica gel eluting with 55, then 10% ethyl acetate in heptane.

1. 5-Benzyloxy-3,4-dichloro5H-furan-2-one. Prepared as provided in Procedure A. 95% yield. ¹H NMR (CDCl₃, 300 MHz) δ 7.41 (br, s, 5H), 5.87 (s, 1H), 4.94 (d, 1H), 4.79 (d, 1H). Elemental Analysis Observed(Theoretical) for $C_{10}H_8Cl_2O_3$: C, 51.12(50.99); H, 2.92(3.11); N, <0.05 (0.00); Cl, 27.19 (27.37).

2. 5-Benzyloxy-3,4-dibromo-5H-furan-2-one. Prepared as provided in Procedure A. 100% yield. ¹H NMR (CDCl₃, 300 MHz) δ 7.41 (br, s, 5H), 5.87 (s, 1H), 4.92 (d, 1H), 4.78 (d, 1H). Elemental Analysis Observed(Theoretical) for $C_{10}H_8Br_2O_3$: C, 38.62(37.97); H, 2.30(2.32); N, <0.05 (0.00); Br, 44.71 (45.92).

Step B: 5-Benzyloxy-3-halo4-isopropyl-5H-furan-2-one.
Alternative 1: Via Cuprate Addition
5-Benzyloxy-3,4-dihalo-5H-furan-2-one (0.03–0.15 mol, 1 equivalent), 1-methyl-2-2pyrrolidinone (NMP) (excess), and copper iodide (1 equivalent) were combined and stirred at room temperature under an inert atmosphere. After about 30 minutes, the resulting tan suspension was cooled to about —15 to about –20° C., and isobutylmagnesium bromide (1.5 equivalents) was added dropwise as a 2.0 M solution in diethyl ether. The reaction mixture was then quenched with a saturated solution of aqueous ammonium chloride, and extracted with methyl tertbutyl ether to provide the crude product as an amber oil. Purification by column chromatography on silica gel eluting with 10% ethyl acetate in heptane provided the product as a colorless oil.
1. 5-Benzyloxy-3chloro4-isopropyl-5H-furan-2-one. 70% yield. MS (AP+) 281.0.
2. 5-Benzyloxy-3-bromo4-isopropyl-5H-furan-2-one. 70% yield. MS (AP+) 325.0.

Alternative 2: Via Suzuki Coupling
5-Benzyloxy-3,4-dihalo-5H-furan-2-one (1 equivalent), 2-methyl-1-propenyl boronic acid (2 equivalents), cesium fluoride (2.5 equivalents, $PdCl_2(PPh_3)_2$ (0.05 equivalent), and triethylbenzyl ammonium chloride (0.05 equivalent) were combined. To this mixture was added a nitrogen-purged toluene and water solvent mixture. The reaction mixture was stirred at room temperature over night and then quenched with 2N aqueous HCl and extracted with 100 mL toluene. The extract was concentrated in vacuo to provide the crude product as a pale orange oil which was purified by column chromatography on silica gel eluting with 10% ethyl acetate in heptane.
2. 5-Benzyloxy-3-bromo4-isopropyl-5H-furan-2-one. 30% yield. MS (AP+) 325.0.

Step C: 5-Benzyloxy-4-isopropyl-dihydro-furan-2one
A mixture of 5-Benzyloxy-3-halo4-isopropyl-5H-furan-2-one (5 mmol, 1 equivalent) and triethyl amine (1.2 equivalents) was dissolved in 65 mL THF. Was transferred to a high pressure reactor. Pd/C (0.3 g) was added, and the mixture was hydrogenated with stirring under 40 pounds per square inch (psi) of hydrogen. The mixture was hydrogenated until hydrogen uptake ceased (about 3 hours). The Pd/C catalyst was filtered out and the solvent was removed in vacuo. The residue was diluted with ethyl acetate, washed with saturated aqueous ammonium chloride and dried over magnesium sulfate. The extract was concentrated in vacuo to give the product as a colorless oil. 1. From 5-Benzyloxy-3-chloro-4-isopropyl-5H-furan-2-one. 38% yield. MS (AP+) 249.1.
2. From 5-Benzyloxy-3-bromo4-isopropyl-5H-furan-2-one. 83% yield. MS (AP+) 249.1

Steps D/E: 3-Aminomethyl-5-methyl-hexanoic acid
5-Benzyloxy-4-isopropyl-dihydro-furan-2-one was hydrogenated in a high pressure reactor as provided above in Step C. Thus, 1.3 g of 5-benzyloxy-4-isopropyl-dihydro-furan-2-one was combined with 1.7 g of ammonium formate, 0.3 g of 20% Pd/C, 1.7 g of ammonium formate and 0.07 g of $[Ir(COD)Cl]_2$ in 25 mL of methanol. The mixture was hydrogenated at 70° C. and 20 pounds per square inch of pressure until hydrogen uptake ceased (about 7 hours) to provide a mixture of 3-Aminomethyl-5-methyl-hexanoic acid (M+160.1) contaminated with 4-isopropyl-pyrrolidin-2-one (M+142.1).
The mixture may be submitted to base hydrolysis to provide exclusively 3-Aminomethyl-5-methyl-hexanoic acid.

Route A', Scheme 1
Step A'. Reductive Amination of Mucohalic Acid with Benzylamine.
Sodium triacetoxyborohydride (6.4 g, 3.0 equivalents) was added slowly to a mixture of mucohalic acid (1 equivalent), acetic acid (0.2 mL) and benzyl amine (1.1 equivalent) in chloroform (50 mL). The reaction mixture was stirred at approximately 25° C. for 24 hours. The reaction mixture was then quenched with water (200 mL) and washed with water (100 mL). The organic layer was dried over magnesium sulfate and concentrated in vacuo to give 1.28g of the product which was further purified by silica gel column chromatograpy to provide the lactam (1.59 g, 66% yield.).

Reductive Amination of Mucochloric Acid with (R)-1-phenylethylamine.
Following the procedure as provided above, provided an 89% yield of the product lactam after purification.

All patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A process for preparing a compound of formula I

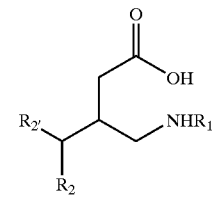

wherein:
$R_1$ is H, $(C_1-C_8)$alkyl, $(C_3-C_7)$cycloalkyl, aryl, $(CH_2)_n$-aryl, heterocyclo, $(CH_2)_n$-heterocyclo, heteroaryl, or $(CH_2)_n$-heteroaryl, wherein n is 0, 1, 2, or 3; and
$R_2$ and $R_{2'}$, are each independently H, straight or branched $(C_1-C_6)$alkyl, a straight or branched $(C_2-C_7)$alkenyl, $(C_3-C_7)$cycloalkyl, alkylcycloalkyl, alkylalkoxy, alkylphenyl, alkyphenoxy, phenyl or substituted phenyl;

comprising:
(a) treating mucochloric or mucobromic acid 1 wherein X is Cl or Br with R'OH, wherein R' is $(C_1-C_6)$alkyl, —$CH_2$-phenyl, or —$CH_2$-substituted phenyl in the presence of acid to provide 2A

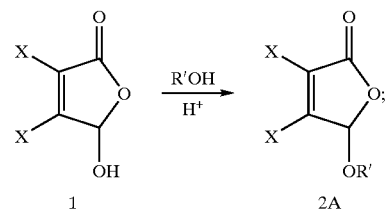

(b) conjugate addition of $R_2R_{2'}CHM_0$ wherein $R_2$ and $R_{2'}$ are as defined above and wherein $M_0$ is MgBr, CuBr, or $B(OH)_2$, to 2A, to provide 3A

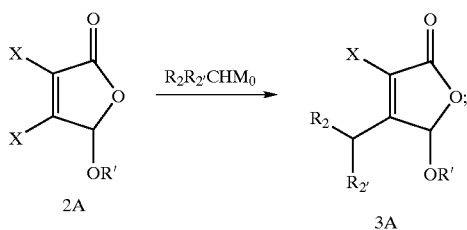

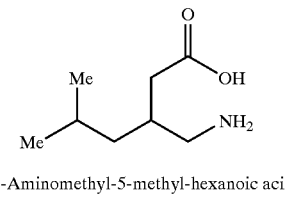

(c) hydrogenation of 3A to provide 4A

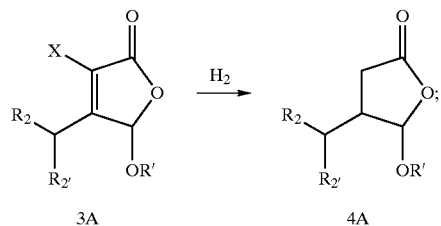

(d) reductive amination of 4A under hydrogenation conditions using ammonium formate or $R_{1a}NH_2$, wherein $R_{1a}$ is H, $(C_1–C_8)$alkyl, $(C_3–C_7)$cycloalkyl, aryl, $(CH_2)_n$-aryl, $(CH_2)_n$—CH—$[(C_1–C_3)alkyl](aryl)$, heterocyclo, $(CH_2)_n$-heterocyclo, heteroaryl, or $(CH_2)_n$-heteroaryl, wherein n is 0, 1, 2, or 3 and p is 0, 1, 2, or 2, followed by hydrolysis

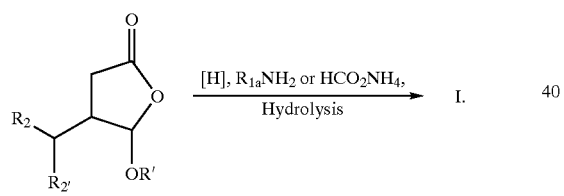

2. The process of claim 1, step (a) wherein R'OH is benzyl alcohol.

3. The process of claim 1, step (b), wherein $R_2R_2CHM_0$ is

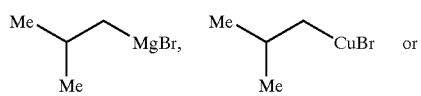

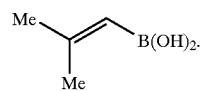

4. The process of claim 1, step (c) using Pd/C as a catalyst in the presence of triethyl amine.

5. The process of claim 1, step (d) wherein the reductive amination is effected under hydrogenation conditions using ammonium formate, triethyl amine, and Pd/C.

6. A process for preparing 3-Aminomethyl-5-methyl-hexanoic acid

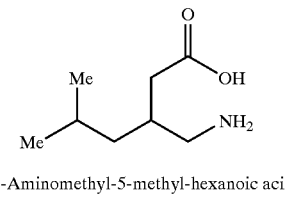

3-Aminomethyl-5-methyl-hexanoic acid comprising:
(a) treating mucochloric or mucobromic acid 1 wherein X is Cl or Br with benzyl amine in the presence of acid, to provide 2

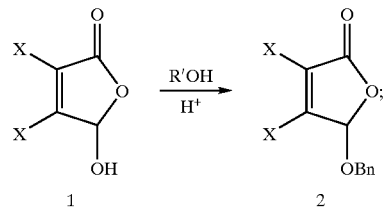

(b) conjugate addition of

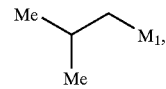

wherein $M_1$ is MgBr, CuBr, or

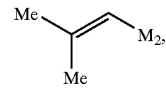

wherein $M_2$ is $B(OH)_2$, to 2 to provide 3B, wherein "- - -" is absent or is a bond;

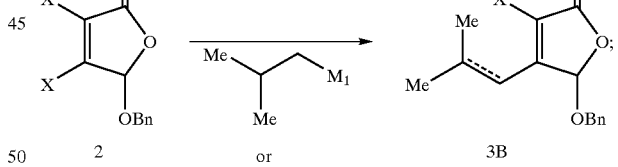

(c) hydrogenation of 3B to provide 4B

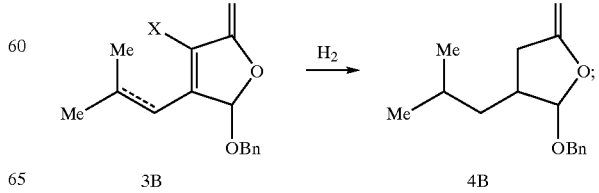

and (d) reductive amination of 4B using ammonium formate, followed by hydrolysis

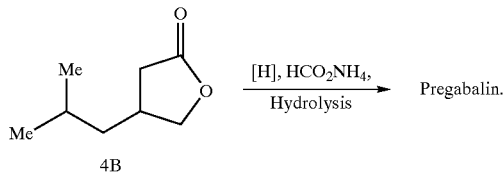

7. A process for preparing a compound of formula I

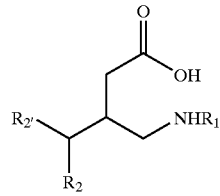

wherein:
R$_1$ is H, (C$_1$–C$_8$)alkyl, (C$_3$–C$_7$)cycloalkyl, aryl, (CH$_2$)$_n$-aryl, heterocyclo, (CH$_2$)$_n$-heterocyclo, heteroaryl, or (CH$_2$)$_n$-heteroaryl, wherein n is 0, 1, 2, or 3; and
R$_2$ and R$_{2'}$ are each independently H, straight or branched (C$_1$–C$_6$)alkyl, a straight or branched (C$_2$–C$_7$)alkenyl, (C$_3$–C$_7$)cycloalkyl, alkylcycloalkyl, alkylalkoxy, alkylphenyl, alkyphenoxy, phenyl or substituted phenyl;

comprising:
(a) reductive amination of mucochloric or mucobromic acid 1 wherein X is Cl or Br, using a reducing agent in the presence of ammonium formate or R$_{1a}$NH$_2$, wherein R$_{1a}$ is (C$_1$–C$_8$)alkyl, (C$_3$–C$_7$)cycloalkyl, aryl, (CH$_2$)$_n$-aryl, (CH$_2$)$_n$—CH—[(C$_1$–C$_3$)alkyl](aryl), heterocyclo, (CH$_2$)$_n$-heterocyclo, heteroaryl, or (CH$_2$)$_n$-heteroaryl, wherein n is 0, 1, 2, or 3 and p is 0, 1, or 2, and an acid catralyst, to provide 2C

[structure 1 → 2C]

(b) conjugate addition of R$_2$R$_{2'}$CHM$_0$ wherein M$_0$ is MgBr, CuBr, or B(OH)$_2$, to 2C to provide 3C

[structure 2A → 3A]

(c) hydrogenation of 3C to provide 4C

[structure 3C → 4C]

and
(d) hydrolysis of 4C

[structure 4C → I]

8. The process of step (a) of claim 7, wherein the R$_{1a}$NH$_2$ is benzylamine or 1-phenylethyl amine.

9. The process of step (a) of claim 7, wherein the reducing agent is selected from sodium triacetoxy borohydride, sodium cyanoborohydride, triethyl silane, Ti(OiPr)$_4$/NaBH$_3$CN, borohydride exchange resin, Zn/acetic acid, sodium borohydride/magnesium perchlorate, or zinc borohydride/zinc chloride.

10. The process of step (a) of claim 7, wherein the reducing agent is sodium triacetoxy borohydride.

11. The process of step (a) of claim 7, wherein the acid catalyst is selected from acetic acid, trichloroacetic acid, trifluoroacetic acid, formic acid, magnesium chloride, magnesium triflate, boron trifluoride etherate, AlCl$_3$, FeCl$_3$, ZnCl$_2$, AlBr$_3$, ZnBr$_2$, TiCl$_4$, SiCl$_4$ and SnCl$_4$.

12. The process of step (a) of claim 7, wherein the acid catalyst is acetic acid.

13. The process of step (a) of claim 7, wherein the stoichiometry of the reaction components is:
(a) 1 equivalents of mucochloric acid;
(b) 1 to 5 equivalents of amine;
(c) 1 to 10 equivalents of reducing agent; and
(d) HOAc sufficient to maintain a pH of about 2 to about 7.

14. The process of step (a) of claim 7, wherein the stoichiometry of the reaction components is:
(a) 1 equivalents of mucochloric acid;
(b) 1 to 3 equivalents of amine;
(c) 1 to 5 equivalents of reducing agent; and
(d) HOAc sufficient to maintain a pH of about 3 to about 6.

15. The process of step (a) of claim 7, wherein the stoichiometry of the reaction components is:
(a) 1 equivalents of mucochloric acid;
(b) 1 to 2 equivalents of amine;
(c) 1 to 3 equivalents of reducing agent; and
(d) HOAc sufficient to maintain a pH of about 4 to about 5.

16. The process of step (a) of claim 7, wherein contacting comprises mixing in a liquid at a sufficient concentration and at sufficient temperatures and for sufficient times to allow formation of the resulting product.

17. The process of claim 16, wherein the liquid is a polar non protic solvent and combinations or mixtures thereof.

18. The process of step (a) of claim 7, wherein the solvent is selected from tetrahydrofuran, acetonitrile, nitromethane, chloroform, methylene chloride, monochloro ethane, 1,1, or 1,2 dichloroethane, 1,1,1 or 1,1,2 trichloroethane, or 1,1,1,2, or 1,1,2,2 tetrachloroethane, or combinations or mixtures thereof.

19. The process of step (a) of claim 7, wherein the temperature is from about −25° C. to about 50° C.

20. The process of step (a) of claim 7, wherein the temperature is from about 0° C. to about 40° C.

21. The process of step (a) of claim 7, wherein the temperature is from about 10° C. to about 30° C.

22. The process of step (a) of claim 7, wherein the temperature is from about 12.5° C. to about 27.5° C.

23. The process of step (a) of claim 7, wherein the time is from about 30 minutes to about 5 days.

24. The process of step (a) of claim 7, wherein the time is from about 1 hour to about 3 days.

25. The process of step (a) of claim 7, wherein the time is from about 6 hours to 48 hours.

26. The process of step (a) of claim 7, wherein the time is from about 12 hours to 36 hours.

27. The process of step (b) of claim 7 wherein $R_2R_{2'}CHM_0$ is

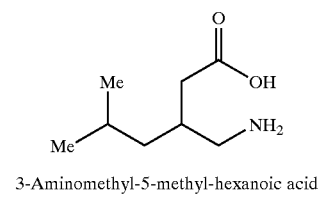

28. The process of step (c) of claim 7 using Pd/C as a catalyst in the presence of triethyl amine.

29. A process for preparing 3-Aminomethyl-5-methyl-hexanoic acid

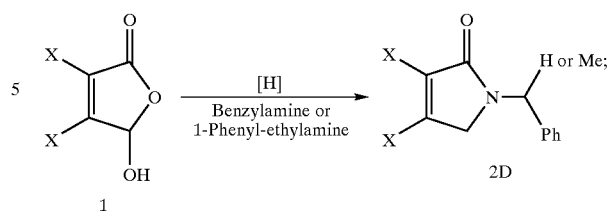

3-Aminomethyl-5-methyl-hexanoic acid comprising:

(a) reductive amination of mucochloric or mucobromic acid 1 wherein X is Cl or Br using sodium triacetoxy borohydride in the presence of benzylamine or 1-phenyl-ethylamine to provide 2D

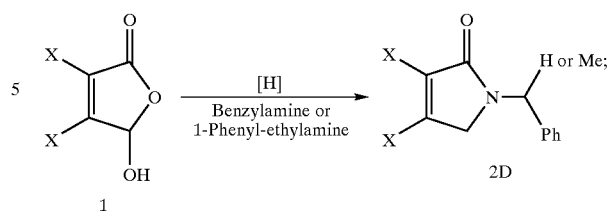

(b) conjugate addition of

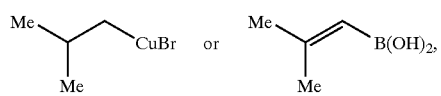

to provide 3D, wherein "- - -" is absent or is a bond;

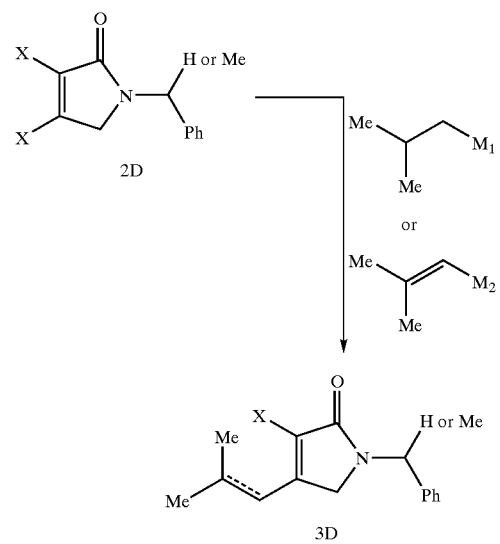

(c) hydrogenation of 3D to provide 4D

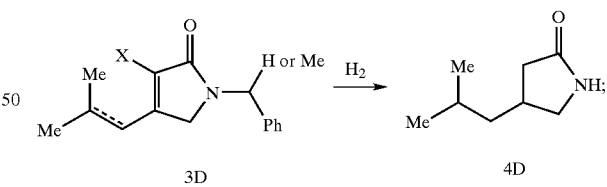

and (d) base hydrolysis of 4D

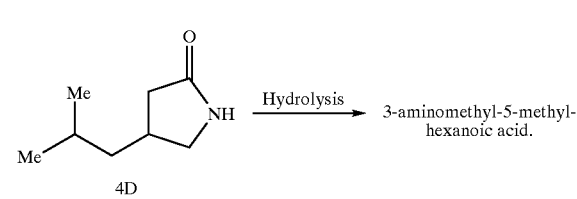

30. A process for preparing 3-aminomethyl-5-methyl-octanoic acid

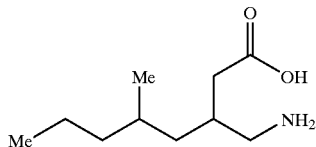

comprising:

(a) treating mucochloric or mucobromic acid 1 wherein X is Cl or Br with R'OH, wherein R' is $(C_1-C_6)$alkyl or —$CH_2$-aryl, in the presence of acid, to provide 2

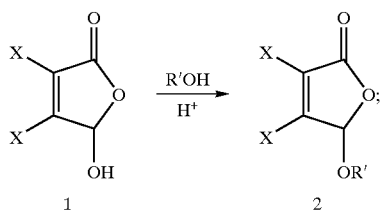

(b) conjugate addition of

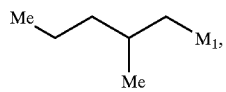

wherein $M_1$ is MgBr, CuBr, or

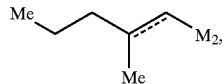

wherein $M_2$ is $B(OH)_2$, to 2 to provide 3BB, wherein "- - -" is absent or is a bond;

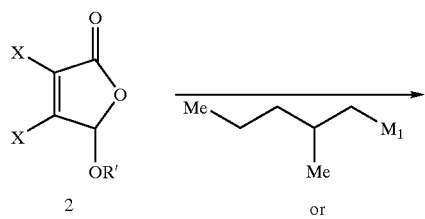

or

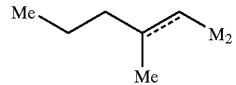

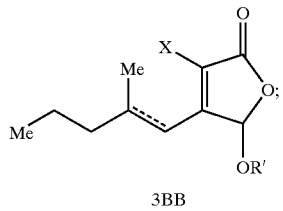

(c) hydrogenation of 3BB to provide 4BB

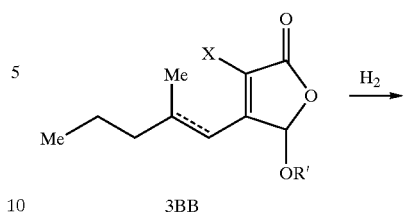

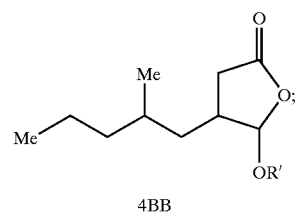

and (d) reductive amination of 4B using ammonium formate, followed by hydrolysis

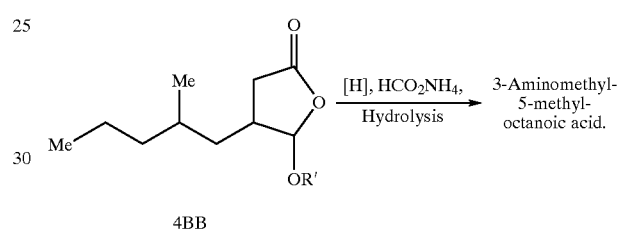

31. A process for preparing 3-aminomethyl-5-methyl-octanoic acid

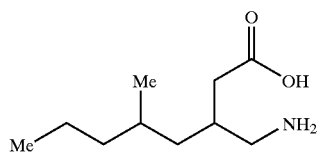

comprising:

(a) reductive amination of mucochloric or mucobromic acid 1 wherein X is Cl or Br using a reducing agent in the presence of benzylamine or 1-phenyl-ethylamine to provide 2D

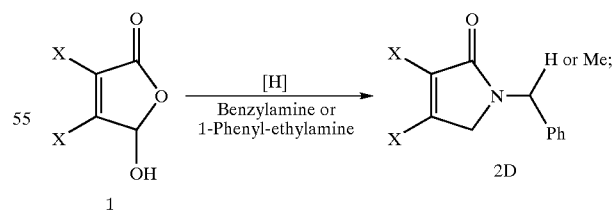

(b) conjugate addition of

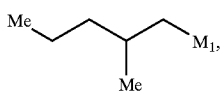

wherein $M_1$ is MgBr, CuBr, or

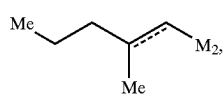

wherein $M_2$ is B(OH)$_2$, to 2 to provide 3DD, wherein "- - -" is absent or is a bond;

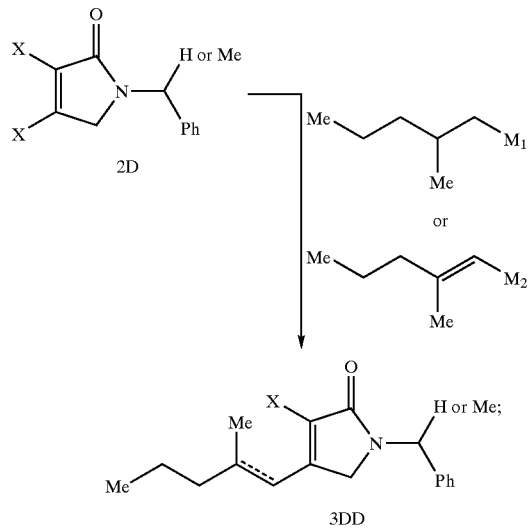

(c) hydrogenation of 3DD to provide 4DD and (d) hydrolysis of 4DD

32. A process for reductively aminating mucohalic acid, comprising:

(a) contacting mucochloric or mucobromic acid 1 wherein X is Cl or Br with sodium triacetoxyborohydride, acetic acid, and $R_3NH_2$, wherein $R_3$ is H, $(C_1-C_8)$alkyl, $(C_3-C_7)$cycloalkyl, aryl, $(CH_2)_n$-aryl, heterocyclo, $(CH_2)_n$-heterocyclo, heteroaryl, or $(CH_2)_n$-heteroaryl, wherein n is 0, 1, 2, or 3; to provide 2E

* * * * *